United States Patent
Puls et al.

(10) Patent No.: US 10,076,486 B2
(45) Date of Patent: Sep. 18, 2018

(54) GEL-LIKE HAIR-SETTING AGENT

(71) Applicant: Henkel AG & Co. KGaA, Duesseldorf (DE)

(72) Inventors: Anna Puls, Winsen (DE); Marcus Noll, Norderstedt (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/345,824

(22) Filed: Nov. 8, 2016

(65) Prior Publication Data

US 2017/0135943 A1    May 18, 2017

(30) Foreign Application Priority Data

Nov. 13, 2015  (DE) .......... 10 2015 222 479

(51) Int. Cl.
| | |
|---|---|
| *A61K 8/89* | (2006.01) |
| *A61K 8/34* | (2006.01) |
| *A61K 8/25* | (2006.01) |
| *A61Q 5/06* | (2006.01) |

(52) U.S. Cl.
CPC .......... *A61K 8/89* (2013.01); *A61K 8/25* (2013.01); *A61K 8/345* (2013.01); *A61Q 5/06* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 2002/0139384 A1* | 10/2002 | Kamis | A61K 8/03 132/202 |
| 2008/0233071 A1* | 9/2008 | Hentrich | A61K 8/25 424/70.122 |
| 2013/0309282 A1 | 11/2013 | Takehana | |
| 2015/0132244 A1 | 5/2015 | Knappe et al. | |
| 2015/0320663 A1 | 11/2015 | Bebot et al. | |

FOREIGN PATENT DOCUMENTS

| | | |
|---|---|---|
| JP | 2011-246352 A | 12/2011 |
| WO | 2013190080 A2 | 12/2013 |
| WO | WO 2014025412 A1 * 2/2014 | ............ A61Q 19/00 |
| WO | 2014/157561 A1 | 10/2014 |

OTHER PUBLICATIONS

WO2014/157561A1 Google English translation, pp. 1-16, ([retrieved from on-line website: http://www.google.as/patents/WO201457561A1?cl=en], last visit Aug. 9, 2017.*
EWG's Skin Deep, "PEG-12", Cosmetics database, pp. 1-2, ([retrieved from on-line website: https://www.ewg.org.skindeep/ingredient/704503/PEG-12]), last visit Aug. 9, 2017.*
UKIPO Combined Search and Examination Report GB1619046.4 Completed: Sep. 22, 2017; dated Sep. 22, 2017 7 pages.

* cited by examiner

*Primary Examiner* — Ernst V Arnold
*Assistant Examiner* — Kyung S Chang
(74) *Attorney, Agent, or Firm* — P. Scott Smith

(57) ABSTRACT

The present invention relates to a silicon dioxide-containing cosmetic composition for hair setting or for the temporary reshaping of keratinic fibers, in particular human hair, which depending on the use enables both a matte and a shiny look and which after application to the hair enables shaping and restructuring of the hairstyle for a long period of time and furthermore forms no visible residues.

13 Claims, No Drawings

GEL-LIKE HAIR-SETTING AGENT

FIELD OF THE INVENTION

The present invention generally relates a cosmetic composition for hair setting or for the temporary reshaping of keratinic fibers, in particular human hair, which depending on the use enables both a matte and a shiny look and which after application to the hair enables a shaping and reshaping of the hairstyle for a long period of time and furthermore forms no visible residues. The present invention relates furthermore to a method for the temporary shaping of keratinic fibers, in particular human hair, in which the cosmetic composition is applied to keratinic fibers.

BACKGROUND OF THE INVENTION

The temporary creation of hairstyles for a longer time period up to a number of days normally requires the use of setting active substances. Hair treatment agents used for a temporary shaping of the hair therefore play an important role. Suitable agents for temporary shaping typically include synthetic polymers and/or waxes as a setting active substance. Agents for supporting the temporary reshaping of hair can be produced, for example, as a hair spray, hair wax, hair gel, or hair foam.

In addition to a high degree of hold, styling agents should satisfy a wide range of further requirements. These can be divided roughly into properties on the hair, properties of the particular formulation, e.g., properties of the foam, gel, or sprayed aerosol, and properties related to the handling of the styling agent, particular importance being attached to the properties on the hair. Mention can be made in particular of humidity resistance, low tackiness (tack), and a balanced conditioning effect. Furthermore, a styling agent should be universally usable, if possible, for all hair types and be gentle to the hair and skin.

In order to satisfy the different requirements, many synthetic polymers for use in styling agents have already been developed as setting active substances. The polymers can be divided into cationic, anionic, nonionic, and amphoteric setting polymers. The polymers when used on hair ideally form a polymer film that, on the one hand, gives the hairstyle a strong hold but, on the other, is sufficiently flexible not to break under stress.

A disadvantage the film-forming polymers, however, is that the films formed after application of the styling agent become brittle under mechanical stress and break, so that the hairstyle hold is lost over time. A styling agent of this kind, after it has dried, allows no permanent restructuring or reshaping of the hairstyle.

Therefore, it was an object of the present invention to provide styling agents with which a long-lasting hairstyle hold can be assured and with which a permanent restructuring of the hairstyle is possible also a long time after the application of the styling agent.

JP 2001-246352 A discloses a styling agent composition that includes hydrophobic silicon dioxide, in addition to other components, in an ethanolic dispersion. The styling agent is sprayed and the ethanol evaporated, the silicon dioxide remaining on the hair as a hairstyle fixative. It has also been reported that the hair can be restructured. It would be desirable, however, to have available styling agents that can be applied in a manner different from spraying. WO 2014/157561 A1 discloses styling agents that include hydrophobic silicon dioxide and a large proportion of water and ethanol in addition to other necessary components.

Known styling agents usually permit the creation of either a rather shiny appearance of the hair or a matte look. Depending on the desired appearance, different products can therefore usually be used. It was a further object of the present invention to provide styling agents that permit the creation of a matte as well as a shiny look.

Furthermore, typical requirements for styling agents such as low or no formation of residues, humidity resistance, low tackiness (tack), and a balanced conditioning effect should be fulfilled.

The above-described objects were achieved surprisingly according to the invention by the compositions disclosed herein.

Furthermore, other desirable features and characteristics of the present invention will become apparent from the subsequent detailed description of the invention and the appended claims, taken in conjunction with this background of the invention.

BRIEF SUMMARY OF THE INVENTION

A cosmetic composition for the temporary reshaping of keratinic fibers that includes: at least one humectant, which is selected from glycerol, at least one polyethylene glycol with 4 to 12 oxyethylene units, and combinations thereof, in a total amount of 1 to 50% by weight; at least one $C_3$-$C_{10}$ alkanediol in a total amount of 5 to 90% by weight; at least one hydrophobic silicon dioxide powder in a total amount of 1 to 10% by weight; and at least one ethoxylated polydialkylsiloxane in a total amount of 0.01 to 10% by weight, where the weight data in each case refer to the total weight of the cosmetic composition.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention provides the following:

A cosmetic composition for the temporary reshaping of keratinic fibers that includes: at least one humectant, which is selected from glycerol, at least one polyethylene glycol with 4 to 12 oxyethylene units, and combinations thereof, in a total amount of 1 to 50% by weight, at least one $C_3$-$C_{10}$ alkanediol in a total amount of 5 to 90% by weight, a) at least one hydrophobic silicon dioxide powder in a total amount of 1 to 10% by weight, at least one ethoxylated polydialkylsiloxane in a total amount of 0.01 to 10% by weight, where the weight data in each case refer to the total weight of the cosmetic composition.

The cosmetic composition according to point 1 that includes, based in each case on the total weight of the cosmetic composition: a total amount of 5 to 30% by weight, preferably 15 to 30% by weight, of the at least one humectant, a total amount of 20 to 80% by weight, preferably 40 to 70% by weight, of the at least one $C_3$-$C_{10}$ alkanediol, a total amount of 2 to 10% by weight, preferably 3 to 8% by weight, of the at least one hydrophobic silicon dioxide powder, and a total amount of 0.02 to 6% by weight, preferably 0.03 to 2% by weight, of the at least one ethoxylated polydialkylsiloxane.

The cosmetic composition according to point 1 or 2, wherein the at least one humectant (a) is selected from glycerol, PEG-4, PEG-6, PEG-8, and combinations thereof and is in particular glycerol.

The cosmetic composition according to one of the preceding points, wherein the at least one $C_3$-$C_{10}$ alkanediol (b) is selected from 1,2-propanediol (propylene glycol), 1,3-propanediol, 1,2-butanediol, 1,3-butanediol, 2-methylpropane-1,2-diol, 1,4-butanediol, 2,3-butanediol, but-2-ene-1,4-diol, neopentyl glycol, 1,2-hexanediol, diethylene glycol (2-(2-hydroxyethoxy)ethanol), and mixtures thereof and is in particular a combination of 1,2-propanediol and 1,3-butanediol.

The cosmetic composition according to point 4, wherein the at least one $C_3$-$C_{10}$ alkanediol (b) is a combination of 1,2-propanediol and 1,3-butanediol and the weight ratio of 1,2-propanediol to 1,3-butanediol is in the range of 40:60 to 60:40.

The cosmetic composition according to one of the preceding points, wherein the hydrophobic silicon dioxide powder (c) is at least one pyrogenic silicon dioxide with a hydrophobically modified surface, preferably hydrophobized pyrogenic silicon dioxide, obtained by treatment of silicon dioxide with hexamethyldisilazane.

The cosmetic composition according to one of the preceding points, wherein the at least one ethoxylated polydialkylsiloxane is selected from ethoxylated polydimethylsiloxanes, in particular polydimethysiloxanes with an average ethoxylation degree of 3 to 17 mol of ethylene oxide, preferably of 10 to 14 mol of ethylene oxide, particularly preferably 12 mol of ethylene oxide. The cosmetic composition according to one of the preceding points that includes furthermore at least one nonionic emulsifier in a total amount of 0.1 to 5% by weight, preferably 0.3 to 3% by weight, based on the total weight of the cosmetic composition.

The cosmetic composition according to one of the preceding points, wherein the composition has a water content of 0 to 10% by weight, preferably 0.1 to 10% by weight, more preferably 0.5 to 7% by weight. The cosmetic composition according to one of the preceding points, wherein the composition includes ethanol in an amount of 0.1% by weight or less. The cosmetic composition according to one of the preceding points, wherein the composition furthermore includes a care component.

The cosmetic composition according to one of the preceding points that includes no additional film-forming polymers, apart from components (a) to (d) and optionally water and an emulsifier. The cosmetic composition according to one of the preceding points, wherein the composition is present as a hair wax, paste, lotion, or clay.

A method for the temporary shaping of keratinic fibers, in particular human hair, in which the cosmetic composition according to one of points 1 to 13 is applied to keratinic fibers. The method according to point 14, wherein the cosmetic composition according to one of points 1 to 13 is applied to damp hair in order to achieve a matte and/or structured look, or the cosmetic composition according to one of points 1 to 13 is applied to dry hair in order to achieve a shiny and/or wet look.

It was found surprisingly that a permanent hold could be achieved with the styling agents of the invention, without film-forming polymers that are typically included in hair gels and other styling agents having to be used. Surprisingly there is additionally an excellent restructurability for a period of up to one day. With the styling agents of the invention, moreover, depending on the use, different appearances of the hair can be achieved, which can vary from a matte, structured look to a shiny, wet look.

Other properties such as a low or no formation of residues, humidity resistance, low tackiness (tack), and a balanced conditioning effect could also be fulfilled.

The styling agents of the invention include no water or only a relatively low proportion of water and based on their consistency and the included main components can be described as oil-gels.

The term "keratinic fibers" according to the invention covers pelts, wool, and feathers but in particular human hair.

The styling agent of the invention includes as component (a) at least one humectant, selected from glycerol, at least one polyethylene glycol with 4 to 12 oxyethylene units, and combinations thereof. The polyethylene glycol preferably includes 4 to 10 oxyethylene units, more preferably 4 to 8 oxyethylene units. The polyethylene glycol can be a mixture of two or more polyethylene glycols. Examples of polyethylene glycols with 4 to 12 oxyethylene units are polyethylene glycols with the INCI names PEG-4 (PEG 200), PEG-6 (PEG 300), PEG-8 (PEG-400), PEG-10, and PEG-12. Preferably, the at least one humectant (a) is selected from glycerol, PEG-4, PEG-6, PEG-8, and combinations thereof, more preferably from glycerol and/or PEG-8, even more preferably glycerol. Glycerol preferably has a purity of 99.0% by weight or higher, even more preferably 99.5% by weight or higher.

The styling agent of the invention includes the at least one humectant (a) in a total amount of 1 to 50% by weight, preferably 5 to 30% by weight, more preferably 10 to 30% by weight, even more preferably 15 to 25% by weight, based on the total weight of the styling agent.

The styling agent of the invention includes as component (b) at least one $C_3$-$C_{10}$ alkanediol, preferably a $C_3$-$C_8$ alkanediol, even more preferably a $C_3$-$C_6$ alkanediol. The alkanediols preferred according to the invention include 1,2-propanediol (propylene glycol), 1,3-propanediol, 1,2-butanediol, 1,3-butanediol, 2-methylpropane-1,2-diol, 1,4-butanediol, 2,3-butanediol, but-2-ene-1,4-diol, neopentyl glycol, 1,2-hexanediol, 1,2-octanediol, diethylene glycol (2-(2-hydroxyethoxy)ethanol), and mixtures thereof. Preferred are 1,2-propanediol and/or 1,3-butanediol, in particular a combination of 1,2-propanediol and 1,3-butanediol.

If a combination of 1,2-propanediol and 1,3-butanediol is included as $C_3$-$C_{10}$ alkanediol (b), it is preferred if the weight ratio of 1,2-propanediol to 1,3-butanediol is in the range of 40:60 to 60:40, preferably about 50:50.

The styling agent of the invention includes the at least one $C_3$-$C_{10}$ alkanediol (b) in a total amount of 5 to 90% by weight, preferably 20 to 80% by weight, more preferably 40 to 75% by weight, even more preferably 60 to 70% by weight, based in each case on the total amount of the styling agent.

At least one hydrophobic or hydrophobized silicon dioxide powder is included furthermore as essential component (c). The use of a hydrophobized pyrogenic silicon dioxide (fumed silica) is preferred according to the invention. The hydrophobizing of the silicon dioxide can occur preferably with hexamethyldisilazane. Named as a preferred example is a hydrophobized pyrogenic silicon dioxide, which was obtained by treatment of silicon dioxide with hexamethyldisilazane (HMDS), in particular of hydrophilic pyrogenic silicon dioxide with a specific BET surface of about 200 to 400 $m^2$/g, more preferably about 300 $m^2$/g. A compound of this type can be obtained commercially under the name Aerosil® R 812 S (Evonik). Further examples of hydrophobic silicon dioxide that can be used with preference are obtainable, for example, under the names Aerosil® R812 S, Aerosil® R 812, Aerosil® R 8200, Aerosil® R 805 (each from Evonik), or HDK® H2000 (Wacker).

The styling agent of the invention includes the at least one hydrophobic silicon dioxide (c) in a total amount of 1 to 10% by weight, preferably 2 to 10% by weight, more preferably 3 to 9% by weight, even more preferably 4 to 8% by weight, based in each case on the total weight of the styling agent. Therefore, a relatively high proportion of the silicon dioxide component is preferred. It is assumed that a high silicon dioxide content, in conjunction with the other components in the given amount ranges, contributes substantially to the surprising and excellent properties.

Lastly, the styling agents of the invention include as a further essential component at least one ethoxylated polydialkylsiloxane (d). The at least one ethoxylated polydialkylsiloxane (d) is preferably selected from ethoxylated polydimethylsiloxanes, in particular polydimethysiloxanes with an average ethoxylation degree of 3 to 17 mol of ethylene oxide, preferably of 10 to 14 mol of ethylene oxide, particularly preferably 12 mol of ethylene oxide. Examples of preferred ethoxylated polydialkylsiloxanes are obtainable under the INCI names PEG-3 Dimethicone, PEG-7 Dimethicone, PEG-8 Dimethicone, PEG-9 Dimethicone, PEG-10 Dimethicone, or PEG-12 Dimethicone. Most preferred according to the invention is PEG-12 Dimethicone (obtainable, e.g., as Xiameter® OFX-0193 Fluid, Dow Corning).

The styling agent of the invention includes the at least one ethoxylated polydialkylsiloxane (d) in a total amount of 0.01 to 10% by weight, preferably 0.02 to 6% by weight, preferably 0.02 to 2% by weight, even more preferably 0.03 to 1% by weight or 0.03 to 0.5% by weight, based in each case on the total weight of the styling agent.

The cosmetic composition of the present invention can be formulated in embodiments without water, therefore with a water content of 0% by weight. The water content is preferably low and is in the range of 0 to 10% by weight, preferably 0.1 to 10% by weight, more preferably 0.2 to 7% by weight, likewise preferably 0.5 to 5% by weight.

It is preferred, furthermore, if the cosmetic composition of the invention includes ethanol in an amount of 0.1% by weight or less and preferably includes no ethanol.

The cosmetic composition of the present invention can include furthermore an emulsifier, in particular in embodiments in which the cosmetic composition includes water. Anionic, cationic, nonionic, and ampholytic surface-active compounds that are suitable for use on the human body and are different from components (a) to (d) may be used in principle as emulsifiers. The ampholytic surface-active compounds comprise zwitterionic surface-active compounds and ampholytes.

The cosmetic composition of the invention preferably includes at least one nonionic emulsifier as an emulsifier. In particular adducts of ethylene oxide to linear fatty alcohols, to fatty acids, to fatty acid alkanolamides, to fatty acid monoglycerides, to sorbitan fatty acid monoesters, to fatty acid glycerides, to methylglucoside monofatty acid esters, and mixtures thereof can be used as nonionic emulsifiers. The nonionic emulsifier is selected particularly preferably from ethoxylated castor oils, in particular ethoxylated, hydrogenated castor oils, more preferably with an average ethoxylation degree of 30 to 60 mol of ethylene oxide. Preferred are PEG derivatives of hydrogenated castor oil, which can be obtained, e.g., under the name PEG Hydrogenated Castor Oil, e.g., PEG-30 Hydrogenated Castor Oil, PEG-33 Hydrogenated Castor Oil, PEG-35 Hydrogenated Castor Oil, PEG-36 Hydrogenated Castor Oil, PEG-40 Hydrogenated Castor Oil, or PEG-60 Hydrogenated Castor Oil. The use of PEG-40 Hydrogenated Castor Oil is preferred according to the invention.

The cosmetic composition of the invention includes the at least one emulsifier that is in particular a nonionic emulsifier, preferably in a total amount of 0.1 to 5% by weight, more preferably 0.3 to 3% by weight, still more preferably 0.5 to 2% by weight.

In embodiments of the invention, the styling agent can include further at least one film-forming polymer. If a film-forming polymer is included, it is included preferably in a small amount. In particularly preferred embodiments of the invention, the styling agent of the invention, however, includes, in addition to the necessary components (a) to (d) and optionally an emulsifier and water, no film-forming polymers, because the disadvantages of film-forming polymers, such as brittleness of the film formed on the hair and an associated low reshapeability, are to be avoided in particular according to the invention.

In embodiments of the invention, the styling agent of the invention can include, in addition to the necessary components (a) to (d) and optionally an emulsifier and water, furthermore a care component, in particular oils, the care components being different from components (a) to (d) and the optionally included emulsifier. If components (a) to (d) and optionally an emulsifier and water are present in the given amounts, however, the presence of a further care component is not necessary, so that in preferred embodiments of the invention no other care components are included.

If a further care component is included, oils suitable according to the invention are selected from the esters of linear or branched, saturated or unsaturated fatty alcohols having 2 to 30 carbon atoms with linear or branched, saturated or unsaturated fatty acids having 2 to 30 carbon atoms, which may be hydroxylated. These include cetyl-2-ethylhexanoate, 2-hexyldecyl stearate (e.g., Eutanol® G 16 S), 2-hexyldecyl laurate, isodecyl neopentanoate, isononyl isononanoate, 2-ethylhexyl palmitate (e.g., Cegesoft® C 24), and 2-ethylhexyl stearate (e.g., Cetiol® 868). Also suitable are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further oils suitable according to the invention are selected from natural and synthetic hydrocarbons such as, for example, from mineral oils, paraffin oils, $C_{18}$-$C_{30}$ isoparaffins, in particular isoeicosane, polyisobutenes and polydecenes, which are obtainable, for example, under the name Emery® 3004, 3006, 3010 or under the name Ethylflo® from Albemarle or Nexbase® 2004G from Nestle, furthermore selected from $C_8$-$C_{16}$ isoparaffins, in particular from isodecane, isododecane, isotetradecane, and isohexadecane, as well as mixtures thereof, and 1,3-di-(2-ethylhexyl)cyclohexane (obtainable, e.g., under the trade name Cetiol® S from BASF).

Further oils suitable according to the invention are selected from benzoic acid esters of linear or branched C8-22 alkanols. Particularly preferred are benzoic acid-C12-C15-alkyl esters, e.g., obtainable as the commercial product Finsolv® TN, benzoic acid isostearyl esters, e.g., obtainable as the commercial product Finsolv® SB, ethylhexyl benzoate, e.g., obtainable as the commercial product Finsolv® EB, and benzoic acid octyldodecyl esters, e.g., obtainable as the commercial product Finsolv® BOD.

Further oils suitable according to the invention are selected from fatty alcohols having 6 to 30 carbon atoms, which are unsaturated or branched and saturated or branched and unsaturated. The branched alcohols are often also referred to as "Guerbet alcohols," since they are obtainable via the Guerbet reaction. Preferred alcohol oils are 2-hexyldecanol (Eutanol® G 16), 2-octyldodecanol (Eutanol® G), 2-ethylhexyl alcohol, and isostearyl alcohol.

Further suitable oils are selected from mixtures of Guerbet alcohols and Guerbet alcohol esters, e.g., the commercial product Cetiol® PGL (2-hexyldecanol and 2-hexyldecyl laurate).

Further cosmetic oils preferred according to the invention are selected from triglycerides (=triesters of glycerol) of linear or branched, saturated or unsaturated, optionally hydroxylated C8-30 fatty acids. The use of natural oils is also suitable, e.g., amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, linseed oil, macadamia nut oil, corn oil, almond oil, manila oil, evening primrose oil, olive oil, palm oil, palm kernel oil, para nut oil, pecan nut oil, peach kernel oil, rapeseed oil, castor oil, sea buckthorn pulp oil, sea buckthorn seed oil, sesame oil, soy oil, sunflower oil, grapeseed oil, walnut oil, wild rose oil, wheat germ oil, and the liquid components of coconut oil and the like. Synthetic triglyceride oils are also suitable, however, in particular capric/caprylic triglycerides, e.g., the commercial products Myritol® 318, Myritol® 331 (BASF), or Miglyol® 812 (Hüls) having unbranched fatty acid esters, as well as glyceryl triisostearin having branched fatty acid groups.

Other cosmetic oils suitable according to the invention are selected from dicarboxylic acid esters of linear or branched C2-C10 alkanols, particularly diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further cosmetic oils suitable according to the invention are selected from the adducts of 1 to 5 propylene oxide units to mono- or polyhydric C8-22 alkanols such as octanol, decanol, decanediol, lauryl alcohol, myristyl alcohol, and stearyl alcohol, e.g., PPG-2 myristyl ether and PPG-3 myristyl ether (Witconol® APM).

Further cosmetic oils suitable according to the invention are selected from adducts of at least 6 ethylene oxide and/or propylene oxide units to mono- or polyhydric C3-22 alkanols such as glycerol, butanol, butanediol, myristyl alcohol, and stearyl alcohol, which can be esterified if desired, e.g., PPG-14 butyl ether (Ucon Fluid® AP), PPG-9 butyl ether (Breox® B25), PPG-10 butanediol (Macol® 57), PPG-15 stearyl ether (Arlamol® E), and glycereth-7 diisonoanoate.

Further cosmetic oils suitable according to the invention are selected from C8-C22 fatty alcohol esters of monovalent or polyvalent C2-C7 hydroxycarboxylic acids, in particular the esters of glycolic acid, lactic acid, malic acid, tartaric acid, citric acid, and salicylic acid. Such esters based on linear C14/15 alkanols, e.g., C12-C15 alkyl lactate, and on C12/13 alkanols, branched in the 2-position, can be obtained under the trademark Cosmacol® from the company Nordmann, Rassmann GmbH & Co., Hamburg, in particular the commercial products Cosmacol® ESI, Cosmacol® EMI, and Cosmacol® ETI.

Further cosmetic oils suitable according to the invention are selected from symmetrical, asymmetrical, or cyclic esters of carbonic acid with $C_{3-22}$ alkanols, $C_{3-22}$ alkanediols, or $C_{3-22}$ alkanetriols, e.g., dicaprylyl carbonate (Cetiol® CC), or the esters according to the teaching of DE 19756454 A1, in particular glycerol carbonate.

Further cosmetic oils, which may be suitable according to the invention, are selected from the esters of dimers of unsaturated $C_{12}$-$C_{22}$ fatty acids (dimer fatty acids) with monohydric linear, branched, or cyclic $C_2$-$C_{18}$ alkanols or with polyhydric linear or branched $C_2$-$C_6$ alkanols.

Further cosmetic oils suitable according to the invention are selected from silicone oils that include, e.g., dialkyl- and alkylarylsiloxanes such as, for example, cyclopentasiloxane, cyclohexasiloxane, dimethylpolysiloxane, and methylphenylpolysiloxane, but also hexamethyldisiloxane, octamethyltrisiloxane, and decamethyltetrasiloxane. Volatile silicone oils, which may be cyclic, can be suitable such as, e.g., octamethylcyclotetrasiloxane, decamethylcyclopentasiloxane, and dodecamethylcyclohexasiloxane, as well as mixtures thereof such as those included, e.g., in the commercial products DC 244, 245, 344, and 345 of Dow Corning. Also suitable are volatile linear silicone oils, in particular hexamethyldisiloxane ($L_2$), octamethyltrisiloxane ($L_3$), decamethyltetrasiloxane ($L_4$), as well as any two- or three-component mixtures of $L_2$, $L_3$, and/or $L_4$, preferably mixtures such as those included, e.g., in the commercial products DC 2-1184, Dow Corning® 200 (0.65 cSt), and Dow Corning® 200 (1.5 cSt) of Dow Corning. Suitable nonvolatile silicone oils are selected from higher-molecular-weight linear dimethylpolysiloxanes, obtainable commercially, e.g., under the name Dow Corning® 190, Dow Corning® 200 Fluid, having kinematic viscosities (25° C.) in the range of 5 to 100 cSt, preferably 5 to 50 cSt, or also 5 to 10 cSt, and dimethylpolysiloxane having a kinematic viscosity (25° C.) of approximately 350 cSt.

The agent can also include as a care substance, for example, at least one protein hydrolysate and/or a derivative thereof. Protein hydrolysates are product mixtures obtained by acid-, base-, or enzyme-catalyzed degradation of proteins. The term "protein hydrolysates" according to the invention is also understood to be total hydrolysates, as well as individual amino acids and derivatives thereof, and mixtures of different amino acids. The molar weight of protein hydrolysates usable according to the invention is between 75 (the molar weight of glycine) and 200,000; the molar weight is preferably 75 to 50,000 daltons, and very particularly preferably 75 to 20,000 daltons.

The agent according to the invention can include further at least one vitamin, provitamin, vitamin precursor, and/or a derivative thereof as a care substance. The vitamins, provitamins, and vitamin precursors that are usually assigned to the groups A, B, C, E, F, and H are preferred according to the invention.

The agents of the invention can include further cosmetically acceptable preservatives. Examples of preferably employed preservatives are 2-phenoxyethanol and/or methylparaben.

The cosmetic composition of the present invention can be produced in forms typical for the temporary reshaping of hair, for example, as a wax, paste, lotion, or clay.

The present invention also relates to a cosmetic, nontherapeutic method for the temporary shaping of keratinic fibers, in particular human hair, in which the cosmetic composition of the invention is applied to keratinic fibers.

The present invention relates furthermore to a method in which the cosmetic composition of the invention is applied to damp hair in order to achieve a matte and/or structured look. The present invention relates furthermore to a method in which the cosmetic composition of the invention is applied to dry hair in order to achieve a shiny and/or wet look.

This different effect depending on the dampness of the hair to which the styling agent of the invention is applied was not to be expected and is to be attributed presumably to the specific composition of the styling agent of the invention.

Overview Table

The composition of some preferred cosmetic agents can be obtained from the following tables (data are given as a solids content and in percentages by weight, based on the total weight of the cosmetic agent, unless otherwise stated).

|  | Formula 1 | Formula 2 | Formula 3 | Formula 4 |
|---|---|---|---|---|
| (a) Glycerol and/or at least one polyethylene glycol with 4 to 12 oxyethylene units | 1 to 50 | 5 to 30 | 10 to 30 | 15 to 25 |
| (b) $C_3$-$C_{10}$ alkanediol | 5 to 90 | 20 to 80 | 40 to 75 | 60 to 70 |
| (c) Hydrophobic silicon dioxide powder | 1 to 10 | 2 to 10 | 3 to 9 | 4 to 8 |
| (d) Ethoxylated polydialkylsiloxane | 0.01 to 10 | 0.02 to 6 | 0.02 to 2 | 0.03 to 1 |
| Misc. | To 100 | To 100 | To 100 | To 100 |

|  | Formula 1a | Formula 2a | Formula 3a | Formula 4a |
|---|---|---|---|---|
| (a) Glycerol and/or PEG-8 | 1 to 50 | 5 to 30 | 10 to 30 | 15 to 25 |
| (b) $C_3$-$C_6$ alkanediol | 5 to 90 | 20 to 80 | 40 to 75 | 60 to 70 |
| (c) Hydrophobic pyrogenic silicon dioxide powder | 1 to 10 | 2 to 10 | 3 to 9 | 4 to 8 |
| (d) Polydimethysiloxanes with an average ethoxylation degree of 10 to 14 mol of ethylene oxide | 0.01 to 10 | 0.02 to 6 | 0.02 to 2 | 0.03 to 1 |
| Misc. | To 100 | To 100 | To 100 | To 100 |

|  | Formula 1b | Formula 2b | Formula 3b | Formula 4b |
|---|---|---|---|---|
| (a) Glycerol | 1 to 50 | 5 to 30 | 10 to 30 | 15 to 25 |
| (b) 1,2-Propanediol and 1,3-butanediol, preferably 60:40 to 40:60 (weight) | 5 to 90 | 20 to 80 | 40 to 75 | 60 to 70 |
| (c) HMDS-treated silicon dioxide, e.g., Aerosil ® R 812 S | 1 to 10 | 2 to 10 | 3 to 9 | 4 to 8 |
| (d) PEG-12 Dimethicone | 0.01 to 10 | 0.02 to 6 | 0.02 to 2 | 0.03 to 1 |
| Misc. | To 100 | To 100 | To 100 | To 100 |

|  | Formula 6 | Formula 7 | Formula 8 | Formula 9 |
|---|---|---|---|---|
| (a) Glycerol and/or at least one polyethylene glycol with 4 to 12 oxyethylene units | 1 to 50 | 5 to 30 | 10 to 30 | 15 to 25 |
| (b) $C_3$-$C_{10}$ alkanediol | 5 to 90 | 20 to 80 | 40 to 75 | 60 to 70 |
| (c) Hydrophobic silicon dioxide powder | 1 to 10 | 2 to 10 | 3 to 9 | 4 to 8 |
| (d) Ethoxylated polydialkylsiloxane | 0.01 to 10 | 0.02 to 6 | 0.02 to 2 | 0.03 to 1 |
| Nonionic emulsifier | 0.1 to 5 | 0.3 to 3 | 0.5 to 2 | 0.5 to 2 |
| Water | 0.1 to 10 | 0.2 to 7 | 0.5 to 6 | 1 to 5 |
| Misc. | To 100 | To 100 | To 100 | To 100 |

|  | Formula 6a | Formula 7a | Formula 8a | Formula 9a |
| --- | --- | --- | --- | --- |
| (a) Glycerol and/or PEG-8 | 1 to 50 | 5 to 30 | 10 to 30 | 15 to 25 |
| (b) $C_3$-$C_6$ alkanediol | 5 to 90 | 20 to 80 | 40 to 75 | 60 to 70 |
| (c) Hydrophobic pyrogenic silicon dioxide powder | 1 to 10 | 2 to 10 | 3 to 9 | 4 to 8 |
| (d) Polydimethysiloxanes with an average ethoxylation degree of 10 to 14 mol of ethylene oxide | 0.01 to 10 | 0.02 to 6 | 0.02 to 2 | 0.03 to 1 |
| Ethoxylated, hydrogenated castor oil, EO 30 to 60 | 0.1 to 5 | 0.3 to 3 | 0.5 to 2 | 0.5 to 2 |
| Water | 0.1 to 10 | 0.2 to 7 | 0.5 to 6 | 1 to 5 |
| Misc. | To 100 | To 100 | To 100 | To 100 |

|  | Formula 6b | Formula 7b | Formula 8b | Formula 9b |
| --- | --- | --- | --- | --- |
| (a) Glycerol | 1 to 50 | 5 to 30 | 10 to 30 | 15 to 25 |
| (b) 1,2-Propanediol and 1,3-butanediol, preferably 60:40 to 40:60 (weight) | 5 to 90 | 20 to 80 | 40 to 75 | 60 to 70 |
| (c) HMDS-treated silicon dioxide, e.g., Aerosil ® R 812 S | 1 to 10 | 2 to 10 | 3 to 9 | 4 to 8 |
| (d) PEG-12 Dimethicone | 0.01 to 10 | 0.02 to 6 | 0.02 to 2 | 0.03 to 1 |
| PEG-40 Hydrogenated Castor Oil | 0.1 to 5 | 0.3 to 3 | 0.5 to 2 | 0.5 to 2 |
| Water | 0.1 to 10 | 0.2 to 7 | 0.5 to 6 | 1 to 5 |
| Misc. | To 100 | To 100 | To 100 | To 100 |

"Misc." according to the invention is to be understood as other conventional components of styling products, for example, perfumes/scents, preservatives, optionally care components. Preferably "Misc." does not include ethanol and film-forming polymers.

Examples

The following styling agents were prepared:

| Component/raw material | INCI | Ex. 1 | Ex. 2 | Ex. 3 | Ex. 4 |
| --- | --- | --- | --- | --- | --- |
| Glycerol 99.5% | Glycerol | 22.0 | — | — | — |
| Polyethylene glycol MW 400 | PEG-8 | — | 20.0 | 20.0 | 28 |
| Propanediol-1,2 | Propylene glycol | 33.25 | 36.85 | 36.95 | 33.6 |
| 1,3-Butylene glycol | Butylene glycol | 33.00 | 33.30 | 33.30 | 30.05 |
| Xiameter OFX-0193 Fluid | PEG-12 Dimethicone | 0.05 | 0.05 | 0.05 | 0.05 |
| Aerosil ® R 812 S | Silica silylate | 5.00 | 9.0 | 9.0 | 7.5 |
| Castor oil hydrog. 40 EO | PEG-40 Hydrogenated Castor Oil | 1.00 | — | — | — |
| Water | Aqua (Water) | 4.00 | — | — | — |
| Perfume | Perfume (fragrance) | 0.70 | — | — | — |
| Euxyl ® K320 | Phenoxyethanol, methylparaben | 1.0 | — | — | — |
| Perfume | Perfume (fragrance) | — | 0.80 | — | 0.8 |
| Perfume | Perfume (fragrance) | — | — | 0.7 | — |
| Total: |  | 100 | 100 | 100 | 100 |

The quantitative data in the tables are given in percentages by weight of the particular raw material, based on the total composition.

The styling agents according to the examples had an oily/gel-like consistency.

The compositions of Examples 1 to 4 were each worked into both still-damp human hair and dry human hair. In each case a matte, structured, or textured look resulted upon application to damp hair. A shiny to wet look resulted upon application to dry hair.

A permanent hold was achieved in all cases. Moreover, in each case there was an excellent restructurability; i.e., the hairstyle could be reshaped even after several hours up to a day and also exhibited a permanent hold thereafter.

Formation of residues was not observed, and humidity resistance, low tackiness (tack), and a balanced conditioning effect were also present.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic composition for the temporary reshaping of keratinic fibers, comprising:
    (a) 15 to 30 wt % of at least one humectant selected from the group consisting of glycerol, at least one polyethylene glycol with 4 to 12 oxyethylene units, and combinations thereof,
    (b) 40 to 70 wt % of at least one $C_3$-$C_{10}$ alkanediol,
    (c) 4 to 8 wt % of at least one hydrophobic silicon dioxide powder,
    (d) 0.01 to 10 wt % of at least one ethoxylated polydialkylsiloxane, and
    (e) 0.5 to 7 wt % of water;
    where the weight data in each case refers to the total weight of the cosmetic composition wherein the cosmetic composition includes 0.1 wt % or less of ethanol and the cosmetic composition does not include film-forming polymers.

2. The cosmetic composition according to claim 1, wherein the ethoxylated polydialkylsiloxane comprises 0.03 to 2% by weight of the cosmetic composition.

3. The cosmetic composition according to claim 1, wherein the at least one humectant (a) is selected from the group consisting of glycerol, PEG-4, PEG-6, PEG-8, and combinations thereof.

4. The cosmetic composition according to claim 1, wherein the at least one $C_3$-$C_{10}$ alkanediol (b) is selected from the group consisting of 1,2-propanediol (propylene glycol), 1,3-propanediol, 1,2-butanediol, 1,3-butanediol, 2-methylpropane-1,2-diol, 1,4-butanediol, 2,3-butanediol, but-2-ene-1,4-diol, neopentyl glycol, 1,2-hexanediol, diethylene glycol (2-(2-hydroxyethoxy)ethanol), and mixtures thereof.

5. The cosmetic composition according to claim 1, wherein the hydrophobic silicon dioxide powder (c) is at least one pyrogenic silicon dioxide with a hydrophobically modified surface.

6. The cosmetic composition according to claim 5, wherein the hydrophobic silicon dioxide powder (c) is a hydrophobized pyrogenic silicon dioxide obtained by treatment of silicon dioxide with hexamethyldisilazane.

7. The cosmetic composition according to claim 1, wherein the at least one ethoxylated polydialkylsiloxane is an ethoxylated polydimethylsiloxanes.

8. The cosmetic composition according to claim 7, wherein the at least one ethoxylated polydialkylsiloxane has an average ethoxylation degree of 3 to 17 mol of ethylene oxide.

9. The cosmetic composition according to claim 7, wherein the at least one ethoxylated polydialkylsiloxane has an average ethoxylation degree of 10 to 14 mol of ethylene oxide.

10. The cosmetic composition according to claim 1, further comprising at least one nonionic emulsifier in a total amount of 0.1 to 5% by weight based on the total weight of the cosmetic composition.

11. The cosmetic composition according to claim 1, further comprising at least one nonionic emulsifier in a total amount of 0.3 to 3% by weight based on the total weight of the cosmetic composition.

12. The cosmetic composition according to claim 1, wherein the composition is a hair wax, a hair paste, a hair lotion, or a hair clay.

13. A method for the temporary shaping of keratinic fibers, comprising applying to the keratinic fibers the cosmetic composition according to claim 1.

* * * * *